(12) United States Patent
Maev et al.

(10) Patent No.: US 8,977,013 B2
(45) Date of Patent: Mar. 10, 2015

(54) BIOMETRIC SENSOR AND METHOD FOR GENERATING A THREE-DIMENSIONAL REPRESENTATION OF A PORTION OF A FINGER

(75) Inventors: Roman Gr. Maev, Windsor (CA); Fedar M. Seviaryn, Windsor (CA)

(73) Assignee: The Institute for Diagnostic Imaging Research, University of Windsor, Ontario (CA)

( * ) Notice: Subject to any disclaimer, the term of this patent is extended or adjusted under 35 U.S.C. 154(b) by 492 days.

(21) Appl. No.: 13/181,402

(22) Filed: Jul. 12, 2011

(65) Prior Publication Data

US 2012/0177257 A1   Jul. 12, 2012

Related U.S. Application Data

(60) Provisional application No. 61/363,386, filed on Jul. 12, 2010.

(51) Int. Cl.
*G06K 9/00* (2006.01)
*A61B 5/117* (2006.01)

(52) U.S. Cl.
CPC ............ *G06K 9/0002* (2013.01); *A61B 5/1172* (2013.01)
USPC ........... 382/124; 382/115; 382/119; 382/126; 382/127; 600/459; 600/445; 600/443

(58) Field of Classification Search
CPC . G06K 9/0002; A61B 8/4483; G01S 15/8947
USPC .......... 382/127, 126, 124, 119, 115; 600/445, 600/443
See application file for complete search history.

(56) References Cited

U.S. PATENT DOCUMENTS 5,224,174 A * 6/1993 Schneider et al. ............. 382/124
5,365,927 A * 11/1994 Roemer et al. ................. 600/410
5,563,345 A * 10/1996 Kersten et al. ................... 73/602

(Continued)

OTHER PUBLICATIONS

"Flashscan 3D" http://www.flashscan3d.com/.

(Continued)

*Primary Examiner* — Vu Le
*Assistant Examiner* — Aklilu Woldemariam
(74) *Attorney, Agent, or Firm* — Carlson, Gaskey & Olds P.C.

(57) ABSTRACT

One embodiment includes a biometric sensor for generating a three-dimensional representation of a portion of a finger, the finger comprising a three-dimensional structure including a surface tissue layer and a subsurface tissue layer, the biometric sensor comprising: a platen; a first transducer; a drive system; a controller; and a software module. The platen is configured to receive the finger. The first transducer is arranged about the platen, configured to scan at least a portion of the finger by transmitting ultrasound waves toward the finger and receiving the ultrasound waves after the waves reflect off of the finger, and further configured to output signals based upon the received ultrasound waves. The drive system is configured to motivate the set of transducers accurately about a central axis substantially parallel to the length of the finger to be scanned. The controller is configured to control the motion of the drive system. The software module is configured to receive a form of the signals from the first transducer and to compose the form of the signals into a three-dimensional representation of at least a portion of the surface tissue layer of the finger.

39 Claims, 5 Drawing Sheets

(56) References Cited

U.S. PATENT DOCUMENTS

| | | | |
|---|---|---|---|
| 5,587,533 A * | 12/1996 | Schneider et al. ............... 73/614 |
| 5,647,364 A * | 7/1997 | Schneider et al. ............ 600/445 |
| 5,689,576 A * | 11/1997 | Schneider et al. ............ 382/124 |
| 5,737,439 A | 4/1998 | Lapsley et al. |
| 5,935,071 A * | 8/1999 | Schneider et al. ............ 600/445 |
| 6,195,448 B1 | 2/2001 | Schiller |
| 6,289,112 B1 * | 9/2001 | Jain et al. ..................... 382/116 |
| 6,296,610 B1 * | 10/2001 | Schneider et al. ............ 600/445 |
| 6,425,870 B1 | 7/2002 | Flesch |
| 6,628,377 B1 | 9/2003 | Sabatini et al. |
| 6,720,712 B2 | 4/2004 | Scott et al. |
| 7,236,616 B1 * | 6/2007 | Scott ............................ 382/124 |
| 7,400,751 B2 | 7/2008 | Schneider et al. |
| 7,558,410 B2 | 7/2009 | Schneider et al. |
| 7,568,391 B2 | 8/2009 | Schneider et al. |
| 7,593,549 B2 * | 9/2009 | Reiner .......................... 382/115 |
| 7,735,729 B2 * | 6/2010 | Rowe ............................ 235/382 |
| 7,739,912 B2 | 6/2010 | Schneider et al. |
| 7,806,852 B1 * | 10/2010 | Jurson ............................ 604/65 |
| 7,817,256 B2 | 10/2010 | Fujii et al. |
| 7,864,306 B2 | 1/2011 | Kono et al. |
| 7,869,624 B2 | 1/2011 | Takiguchi |
| 7,916,907 B2 | 3/2011 | Beatson et al. |
| 7,946,989 B2 | 5/2011 | Hasegawa et al. |
| 7,953,259 B2 | 5/2011 | Mcclurg |
| 8,229,177 B2 * | 7/2012 | Duffy et al. ................... 382/115 |
| 2003/0069502 A1 * | 4/2003 | Makin et al. ................... 600/437 |
| 2005/0117786 A1 * | 6/2005 | Schneider et al. ............ 382/124 |
| 2005/0238212 A1 * | 10/2005 | Du et al. ....................... 382/124 |
| 2006/0115132 A1 * | 6/2006 | Schneider et al. ............ 382/126 |

OTHER PUBLICATIONS

"Touchless Biometric System" http://www.tbsinc.com/.

* cited by examiner

BIOMETRIC SENSOR AND METHOD FOR GENERATING A THREE-DIMENSIONAL REPRESENTATION OF A PORTION OF A FINGER

CROSS-REFERENCE TO RELATED APPLICATIONS

This application claims the benefit of U.S. Provisional Application No. 61/363,386 filed 12 Jul. 2010, which is incorporated in its entirety by this reference.

BACKGROUND

Fingerprint imaging, based on unique fingerprint patterns to distinguish between individuals, is a common form of identification. Fingerprints are useful identifiers for a variety of applications, such as restricting access of protected areas and data to approved individuals. A traditional method of obtaining fingerprint images is blotting the pad of a fingertip with ink and imprinting the inked pattern on a piece of paper, and the resulting two-dimensional image may be scanned and stored into a database for easy access. Another typical method of obtaining fingerprint images is pressing the pad of a fingertip on a platform of a fingerprint scanner to obtain a two-dimensional image of the fingerprint. To identify an individual, his or her fingerprint is obtained and then compared to the stored fingerprint image. However, these conventional methods are not foolproof and may be deceived by, for example, copying the outer surface tissue of a finger with a mold. Thus, there is a need in the biometric identification field to create an improved fingerprint imaging system. This invention provides such an improved biometric sensor.

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
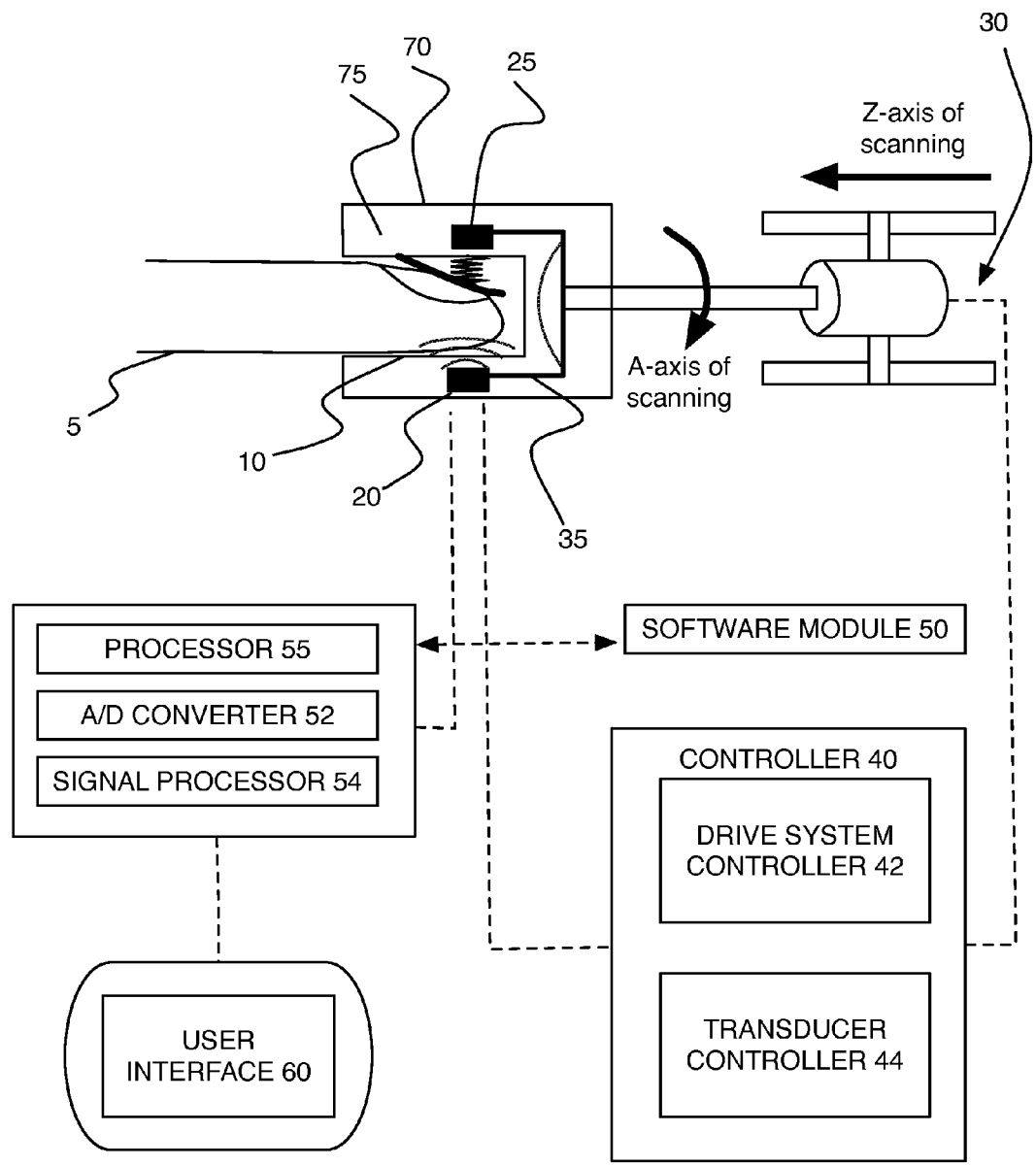
FIG. 1 is a schematic of the biometric sensor of a preferred embodiment.
Figure 5:
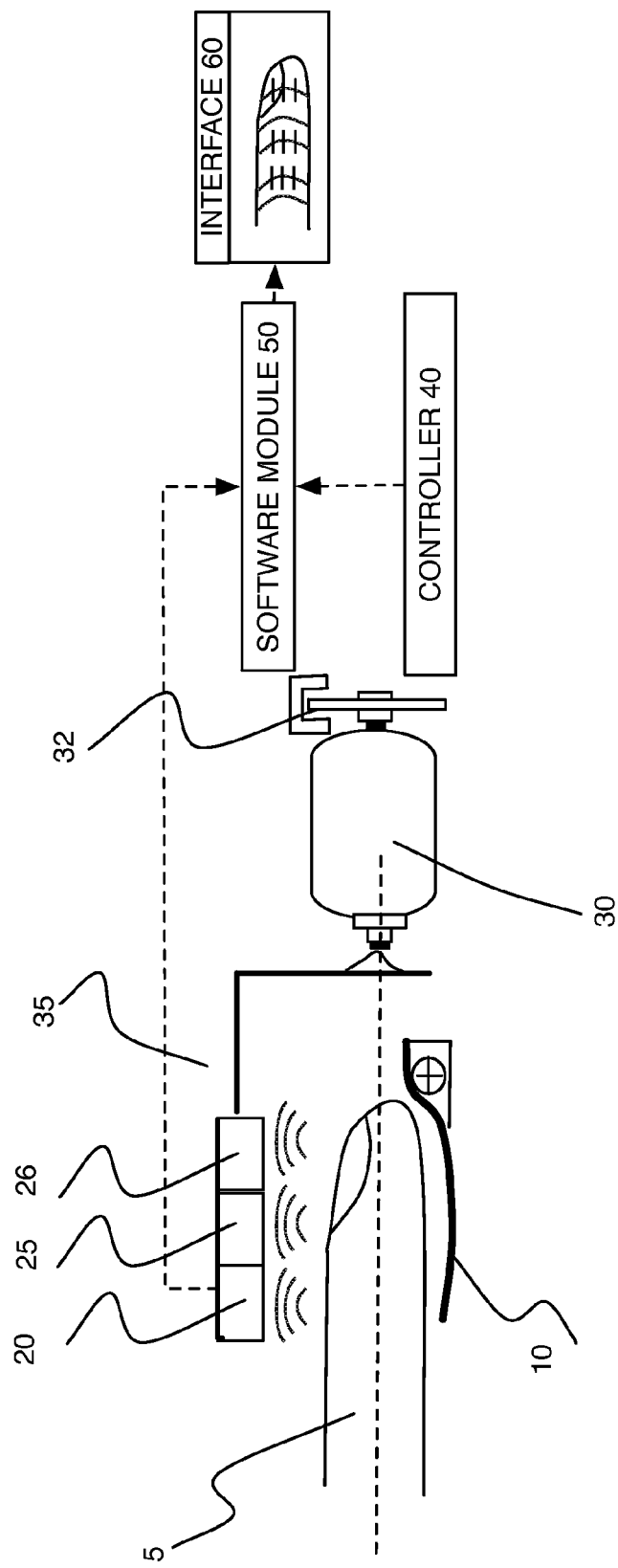
FIG. 5 and 6 are schematics of the biometric sensor of a preferred embodiment.
Figure 6:
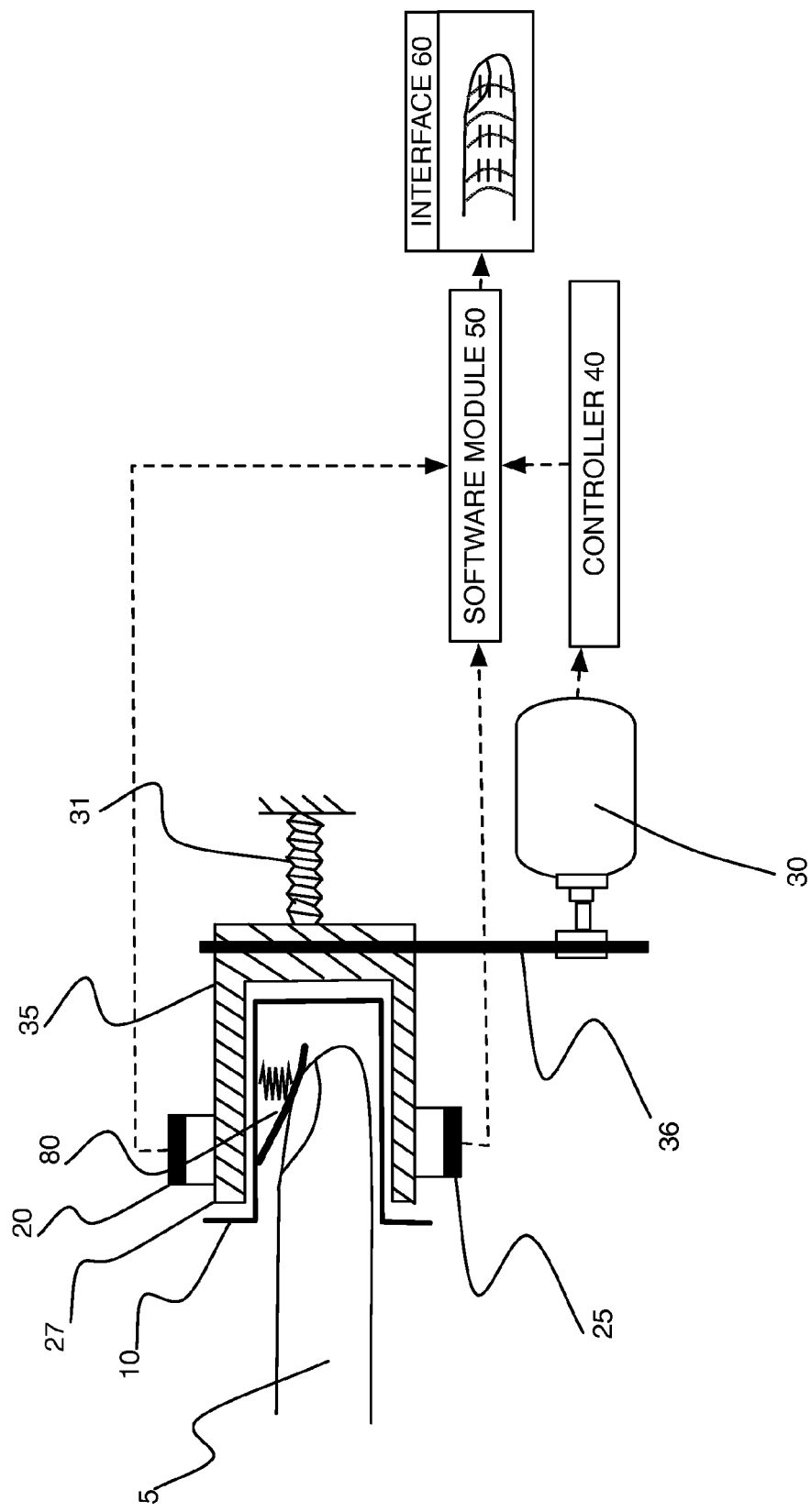

As shown in FIGS. 1, 5, and 6, the biometric sensor of the preferred embodiment functions to scan a finger 5, wherein the finger comprises a surface tissue layer and at least one subsurface tissue layer. The biometric sensor of the preferred embodiment includes a platen 10 that receives a finger 5; a first transducer 20 arranged around the platen 10 that receives ultrasound waves after the ultrasound waves reflect off of the finger 5 and outputs signals based upon the received ultrasound waves; a drive system 30 that motivates first transducer 20 arcuately about a central axis substantially parallel to the length of the finger to be scanned; a controller 40 that controls the motion of the drive system 30 and thus the position of the first transducer 20; and a software module 50 that composes a form of the signals into a three-dimensional representation of the finger 5. The biometric sensor preferably comprises a set of transducers is preferably, including the first transducer 20 and a second transducer 25; however, the system may comprise any other number of transducers. The biometric sensor may further include a user interface 60 that presents instructions and/or the representation of the finger to a user. A housing 70 defining an enclosed internal space may also be included, wherein the internal space is filled with a coupling liquid 75 that improves the propagation of ultrasound waves between the finger 5 and first transducer 20. A rotor 35 may communicate motion of the drive system 30 to the first transducer 20, and the biometric sensor may further include a biased element 80 that stabilizes the finger 5 such that motion of the finger 5 is minimized during the scanning process. The biometric sensor preferably uses high frequency acoustic microscopy technique to collect data from the surface tissue layer and at least one subsurface tissue layer of the finger 5 and to generate a representation of the finger 5 including a large amount of detail appropriate for an identification process based upon the data. The representation may be a volumetric (i.e. substantially circumferential) three-dimensional representation of the finger 5, a two-dimensional image of a fingerprint, an image of selected skin and subsurface skin layer features, or any suitable representation of at least a portion of the finger 5. The system is preferably used for obtaining one or both of an initial representation of the finger 5 and any number of identifier representations that may be compared to the initial representation, such as for identification purposes. By including a large amount of detail in the representation of the finger 5, the biometric sensor preferably facilitates an identification system that is more difficult to deceive and has increased accuracy (fewer "false positives" and "false negatives"). For example, the biometric sensor may be used to create a more robust security system for restricting access to locations or data. However, the biometric sensor may additionally and/or alternatively be used in any suitable application, such as identification of criminals by law enforcement. The system is preferably used to generate a representation of one or more fingers, but may alternatively be adapted to generate representations of other suitable body parts, such as a hand, face, toe, or foot, or other objects substantially cylindrical in cross-section.

The platen 10 of the preferred embodiment functions to support the finger 5. Prior to use, a user disposes the finger 5 onto the platen 5, wherein the platen 10 locates the finger 5 in an appropriate position such that a desired portion of the finger 5 may subsequently be scanned. In a variation of the invention in which only the portion of the finger past the distal knuckle is scanned, the platen 10 preferably comprises a concave surface defining a substantially shallow recess that cups the pad of the finger 5 from the tip of the finger to the distal knuckle, as shown in FIG. 5. In a variation in which the substantially full length of the finger 5 is scanned, the platen 10 preferably comprises an elongated concave surface that cups the finger 5 from the tip of the finger to the proximal knuckle. However, the platen 10 may be a sufficiently planar surface, a polyhedronal surface, or any other suitably-shaped surface. Furthermore, the platen 10 may support any suitable portion of the finger 5 and/or portion of the hand to which the finger is appended. The platen 10 is preferably comprised of an ultrasonically-transparent material such as polystyrene or any other suitable material. Furthermore, the platen 10 is preferably of a geometry such that fingers of nearly all sizes may be disposed on the platen 10 during the scanning procedure; however, the platen 10 may only be compatible with fingers of a certain size range, such as fingers of infants or fingers of typical males ages twenty to thirty.

The biased element 8o, which is arranged substantially proximal the platen 10, functions to stabilize the finger 5 on the platen 10 such that motion of the finger 5 is minimized during the scanning process. The stability of the finger 5 during the scanning process can affect the quality of the image generated by the biometric system since the ultrasound waves interacting with the finger 5 are received by the first transducer 20 over a period of time. Therefore, the biometric sensor preferably incorporates the biased element 80. The biased element may be a tab that pivots on one end and is persuaded over the finger 5 on the opposite end by a spring, as shown in FIGS. 1 and 6. Alternatively, the biased element 80 may be a pincer with prongs that engage the finger 5 during the scan such that the finger cannot be removed from the platen 10 during scanning. However, the biased element 80 may be any other type of mechanism that stabilizes the finger 5 on the platen 10.

The first transducer 20 of the preferred embodiment functions to receive ultrasound waves after the ultrasound waves have reflected off of the finger 5 and to output signals based upon the received ultrasound waves. The first transducer 20 is preferably a focused piezoelectric transducer, but the first transducer 20 may comprise any other transducer capable of receiving an ultrasound wave and outputting a signal based upon the received ultrasound wave, such as a magnetostrictive transducer, electrodynamic transducer, MEMS transducer, or any other type of transducer. In a first variation of the first transducer 20, the first transducer 20 is configured only to receive ultrasound waves; in a second variation, the first transducer 20 is configured to generate and receive ultrasound waves. In the first variation, a second transducer 25 arranged substantially proximal the first transducer 20 preferably generates the ultrasound waves, wherein the ultrasound waves reflect off of the finger 5 and are then received by the first transducer 20. In the second variation, the first transducer 20 generates the ultrasound waves for a first period of time and then receives the ultrasound waves for a second period of time. Preferably, the ultrasound waves are generated at a predetermined frequency. The first transducer 20 of the preferred embodiment functions to collect acoustic data that is representative of the finger surface and subsurface skin layers and that may be used to create a representation of the finger 5. The first transducer 20 emits ultrasound waves at a predetermined frequency and receives ultrasound data resulting from ultrasound waves interacting with tissue of the finger 5. The emitted ultrasound waves may reflect off layers of tissue, transmit through tissue, be scattered by tissue, and/or interact with the tissue in any manner. The first transducer 20 receives the ultrasound waves after interaction with the finger 5 and subsequently generates signals that are based on the interaction and are thereby representative of the finger surface and subsurface tissue layers. The received ultrasound waves preferably map and represent tissue including the dermis, the fingerprint groove pattern, and a subskin area up to approximately 3 mm depth or any suitable depth below the skin surface. The subskin portion of the ultrasound data may include muscle structure, blood vessel networks, and/or any suitable anatomic or physiological features that may be unique to an individual and therefore useful for identification purposes. The ultrasound data may also include cardiovascular information that indicates whether the person is alive, which may be useful against deception such as an unauthorized person using the finger of a deceased authorized individual; this may be achieved through various methods such as Doppler detection of blood movement. In some embodiments, the system may additionally and/or alternatively include an infrared radiation sensor to gather data representing the heat signature of an individual, and/or other suitable kinds of sensors.

Figure 2:
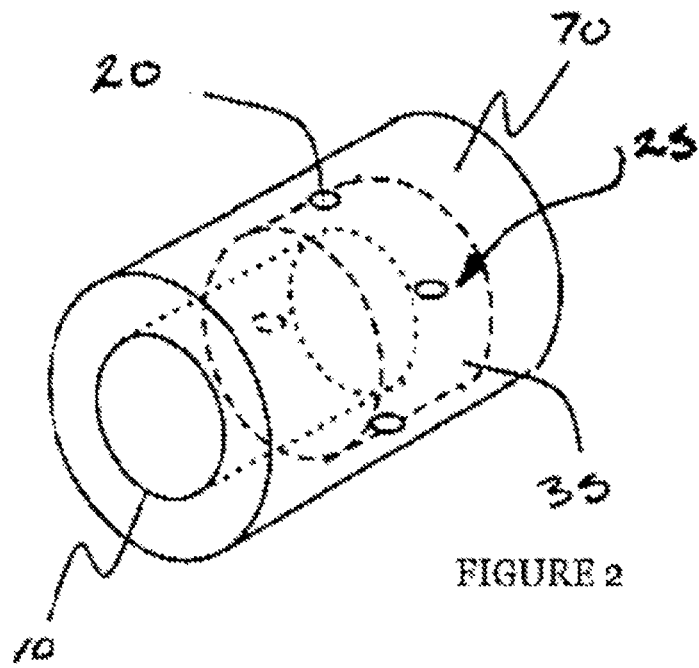
FIG. 2 is schematic of the housing, set of transducers, and rotor of the biometric sensor of a preferred embodiment.

In a variation of the preferred embodiment, the biometric sensor comprises a plurality of transducers, such as the first transducer 2 and a second transducer 25. The plurality of transducers may be identical but may also be substantially dissimilar. The transducers are preferably arranged around the rotor 35 with uniform spacing such that the transducer arrangement is radially symmetric about the central axis of the rotor 35. As shown in FIG. 2, the set of transducers may include two pairs of identical ultrasound transducers arranged opposite each other, such that four transducers are arranged every 90 degrees around the circumference of the rotor 30 and/or around the platen 10; however, the set of transducers may alternatively include any suitable number and/or kind of transducers arranged in any suitable arrangement. Multiple transducers help to reduce overall scanning time required to image the entire inserted finger. The ultrasound data is preferably transmitted in the form of electrical signals to the software module with wireless or other non-contact means, since the rotor and the transducers are moving relative to the platen 10 and a wired signal transmission may become kinked or tangled, but the signals may be transmitted in any other suitable manner. Each transducer is preferably a focused piezoelectric transducer that is controlled to emit and receive converging beams of ultrasound waves at a predetermined frequency, and more preferably ultrasound waves having a frequency of approximately 50 MHz, but each transducer may alternatively receive and/or emit ultrasound waves having any suitable frequency.

Figure 3A:
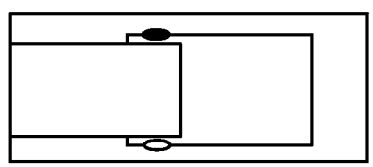
FIG. 3 is a schematic of the operation of the drive system by the controller of the biometric sensor of a preferred embodiment.
Figure 3B:
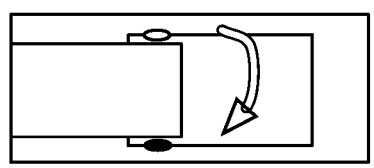
Figure 3C:
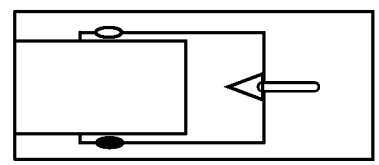

The drive system 30 of the preferred embodiment functions to actuate the first transducer 20 during the scan of the finger 5 disposed on the platen 10. As shown in FIG. 1, the drive system 30 is preferably a bidirectional drive system that includes at least two actuators such that the drive system actuates the first transducer 20 in at least two degrees of freedom. One degree of freedom of the first transducer 20 is preferably a Z-axis translation linearly along a central axis that is substantially parallel to the axis of the finger 5 and is preferably provided by a first linear actuator. The second degree of freedom of the first transducer 20 is preferably an A-axis rotation about the central axis and preferably provided by a second rotary actuator. In this first preferred embodiment, the first and second actuators may operates synchronously and concurrently to motivate the first transducer 20 arcuately about the finger 5 in a spiral path. Alternatively, the linear actuator may drive the first transducer 20 linearly along the Z-axis to a first position (shown in FIG. 3A), at which point the rotary actuator motivates the first transducer 20 arcuately about the A-axis such that the first transducer 20 receives ultrasound waves from at least a portion of a first circumference of the finger (shown in FIG. 3B); subsequently, the linear actuator may drive the first transducer 20 linearly along the Z-axis to a second position (shown in FIG. 3C), at which point the rotary actuator motivates the first transducer 20 arcuately about the A-axis such that the first transducer receives ultrasound waves from at least a portion of a second circumference of the finger. In this variation, the first transducer 20 follows a series of linear and arcuate paths. In a second preferred embodiment, the Z-axis translation and A-axis rotation are provided by a single rotary actuator, as shown in FIG. 6. In this variation, a lead screw 31 may drive the transducer linearly as a rotary actuator of the drive system 30 motivates the first transducer 20 arcuately about the finger 5; in this variation, the first transducer 20 is effectively motivated in a spiral path. In another variation of the drive system 30, as shown in FIG. 5, a single rotary actuator motivates the first transducer 20, the second transducer 25, and a third transducer 26 concurrently about the finger 5, wherein the first, second, and third transducers are arranged linearly substantially in line with the axis of the finger 5 such that the transducers receive ultrasound waves that reflect off of the finger 5 along the length of the finger 5; any number of transducers may be used in this configuration of the drive system 30. However, the drive system 30 may comprise: any combination of linear and/or rotary actuators; any type of actuator, including DC electric motors, stepper motors, air motors, or any other type of motor; as well as any other type of motion transmission device, including a planetary gearboxes, linear slides, lead screws, or any other type of motion transmission device. Furthermore, the drive system 30 may motivate any number of transducers, either independently or concurrently.

The encoder 32, which is preferably connected to the drive system 30, functions to determines the arcuate and/or linear position of the first transducer 20 relative to the platen 10, relative to an actuator, or relative to any other element of known position and/or index. The encoder 32 may be used to provide feedback to the controller 40 such that the motion (e.g. velocity or position) of the first transducer 20 by the drive system 30 is appropriately maintained. The encoder 32 may also or alternatively communicate with the software module 50 such that a signal from the first transducer 20 may be linked to a position of the first transducer 20; this may be particularly useful in manipulating the signals into a two- and/or three-dimensional image of the finger 5, wherein the position of the first transducer 20 when an ultrasound wave is received must be known in order to properly assemble the signals into an image. However, any number of encoders may be used to determine the linear and/or arcuate position of any number of transducers of the biometric sensor; the encoders may be arranged in any suitable manner, such as connected to an output shaft of an actuator of the drive system 30 or mounted on the rotor 35 on which any number of transducers are arranged.

The housing 70, which comprises a recess arranged about the platen 10, functions to house the first transducer 20. The housing 70 preferably protects the first transducer 20 from impact, such as by the finger 5 as the finger 5 is placed on or removed from the platen 10. The housing 70 preferably includes an inner wall arranged about the platen 10 and an outer wall defining a hollow internal space located between the inner wall and the outer wall. A portion of the inner wall of the housing 70 may further define the platen 10, as shown in FIG. 1. The outer wall of the housing 70 is preferably substantially cylindrical and substantially parallel to the inner wall, thereby forming an annular hollow internal space between the inner and outer walls, although the outer wall may have any suitable shape. The housing 70 preferably functions to provide structural support for at least a portion of the biometric sensor and the finger 5; for example, the outer wall of the housing 70 may have a flat side to enable the housing 70 to rest stably on a flat surface and the finger 5 to rest stably on the platen 10. Alternatively, the housing 70 may be adapted to rest in a support such as a cradle or to mount on a wall or other surface. The housing 70 may rest or be mounted on a surface such as a table or wall during scanning of the finger 5, or may be handheld and carried up to the finger 5. The biased element 80 may be mounted on the housing 70 such that the biased element 80 contacts and stabilizes the finger against a particular side of the platen 10, which may help to maintain consistency between fingerprint images and to reduce motion artifacts in the images. For example, as shown in FIG. 1, a biased sprung platform may encourage an inserted finger towards a lower surface of the platen 10. The housing 70 may have guiding features such as markings or a track to further position the finger when inserted onto the platen 10; this may further help maintain consistency between fingerprint images. The housing 70 is preferably made of plastic and constructed by injection molding, but may alternatively be made of metal or any suitable material and through any suitable manufacturing process such as milling, turning, or spinning.

The first transducer 20 is preferably arranged within the internal space of the housing 70 such that the first transducer 20 may be motivated linearly and arcuately within the internal space and about the finger 5. The internal space of the housing 70 is preferably filled with a coupling liquid 75, as shown in FIG. 1, wherein the coupling fluid 75 improves propagation of ultrasound waves from the finger 5 to the first transducer 20. The coupling fluid 75 may be any suitable fluid, such as mineral oil, degassed water, white petrolatum, or any other suitable coupling fluid such that appropriate transmission, attenuation, refection coefficient, and/or acoustic impedance of the coupling fluid 75 is achieved without substantially impeding the motion of the first transducer 20 within the housing 70. Because the propagation of ultrasound waves through the coupling fluid 75 may change with temperature, the housing 70 may further comprise a temperature sensor that monitors the temperature of the coupling fluid 75 such that the propagation properties of the biometric sensor may be taken into account by the software module 50 when the image of the finger 5 is assembled from signals from the first transducer 20. The level of coupling fluid 75 within the internal space is preferably such that the first transducer 20 remains consistently submersed in the coupling fluid 75 through the entire motion of the first transducer 20 within the housing 70. The biometric sensor preferably further comprises a sliding seal 37 that seals the coupling liquid within the internal space between the platen and the transducer. The seal 37 preferably does not impede the motion of the rotor 35 and the first transducer 20 (and second transducer 25) but rather prevents liquid from escaping the internal space. The seal may comprise one or more o-rings of any cross-sectional shape (such as round, square, ovular, or any other shape), a velvet seal, a grease seal, or any other type of seal.

The rotor 35, which is connected to at least one element of the drive system 30, functions to communicate motion of the drive system 30 to the first transducer 20. The rotor preferably rotates and moves linearly within the internal space of the housing 70 such that the first transducer 20 is motivated arcuately around and axially along the platen 10. In the variation of the invention that incorporates a coupling fluid 75 in the housing 70, the rotor is preferably hermetically enclosed in the internal space of the housing such that the coupling fluid 75 cannot escape the housing 70. The rotor 35 may comprise a cylindrical barrel upon which the first transducer 20 or multiple transducers are arranged, as shown in FIG. 1. Alternatively, the rotor 35 may be one or several arms extending along the length of the finger, such as shown in FIG. 5, such that at least one transducer may be arranged on each arm. The rotor 35 may be rigidly connected to the drive system 30, such as shown in FIG. 1, or softly connected to the drive system 30, such as with a belt 36 as shown in FIG. 6. However, the rotor 35 may be of any other suitable material and/or suitable geometry and connected to the drive system 30 by any other suitable means.

The controller 40 of the preferred embodiment functions to control the operation of the drive system 30 and the first transducer 20 or set of transducers. As shown in FIG. 1, the controller preferably includes a drive system controller 42 and a transducer controller 44. The drive system controller preferably coordinates the Z-and A-axis degrees of freedom in a fast scanning manner to allow the first transducer 20 or set of transducers to cover the entire finger surface enclosed by the housing 70 (or a significant portion of the finger 5 that is within the range of the drive system 30). In one embodiment with the transducers aligned in a first plane normal to the axis of the platen 10, such as in FIG. 2, the drive system controller 42 operates the rotor 35 at least a portion of a full rotation in the A-direction (FIGS. 3A and 3B), then operates the linear actuator in the Z-direction such that the transducers are aligned in a second plane parallel to the first plane (FIG. 3C), and repeats these steps for additional planes until the set of transducers have covered a required area of finger surface with the sum of planes or "slices". Each additional plane is preferably immediately adjacent to the previous plane, but some or all of the planes may alternatively be spaced apart to create a partial representation of the finger 5 with images that are spaced apart at selected locations along the finger 5. Each rotation of the rotor 35 within a plane may be a full rotation, or a portion of a rotation that may depend on the number of transducers arranged on the rotor 35. For example, for the rotor 35 having four transducers configured to send and receive ultrasound waves and arranged every 90 degrees around the circumference of the rotor 35, the drive system controller 42 may operate the rotor 35 for a quarter (90 degrees) of a complete rotation for each slice to allow the four transducers to collectively sweep the entire finger 5 within that slice. As another example, for a rotor having two transducers configured to send and receive ultrasound waves and arranged opposite to one another around the rotor 35, the drive system controller 42 may operate the rotor 35 for half of a complete rotation (180 degrees) for each slice. In another variation, each plane or slice scanned by the set of transducers is at a non-perpendicular angle with respect to the central axis of the platen 10. In yet another variation, the drive system controller 42 moves the rotor 35 in the Z-direction longitudinally along the platen 10 for a first longitudinal scanning pass along at least a portion of the length of the finger 5, then rotates the rotor 35 incrementally and makes a secondary longitudinal scanning pass (in the same direction as the first longitudinal scanning pass, or in the opposite direction as the first longitudinal scanning pass in a S-shaped pattern), and repeats these steps for additional longitudinal passes. However, the drive system controller may control the drive system to operate in any suitable manner, such as actuating the set of transducers in a spiral path. Preferably, the transducer controller 44 controls the generation of ultrasound waves and the collection of the ultrasound waves after the ultrasound waves interact with the finger 5. The transducer controller 44 preferably includes instrumentation that generates short pulses to periodically excite the first transducer 20 or set of transducers (or other suitable trigger for activating the transducers), such that the first transducer 20 or set of transducers is coordinated in emitting ultrasound waves at a predetermined frequency and receiving ultrasound waves that have reflected off of the finger 5. The transducer controller 44 also preferably performs timely-coordinated electronic switching between the transducers, such as with a multiplexor. In the variation in which the first transducer 20 is configured to receive ultrasound waves and the second transducer 25 is configured to generate ultrasound waves, the transducer controller 44 may operate the second transducer 25 to generate ultrasound waves at a preselected frequency and configure the first transducer 20 to receive the ultrasound waves after the ultrasound waves interact with the finger 5. Alternatively, in the variation in which the first transducer 20 is configured to generate and to receive ultrasound waves, the transducer controller 44 may operate the first transducer 20 in an ultrasound wave generation mode for a first period of time and then switch the first transducer 20 to an ultrasound wave collection mode for a second period of time. Preferably, the transducer controller 44 also provides power to the first transducer 20 or set of transducers, such as through a wired connection. In the variation of the invention in which the first transducer 20 is motivated in a spiral pattern about the platen 10 and produces and/or receives electrical signals that are communicated to and/or from the transducer controller 44, the wired electrical connection may comprise at least one slip ring such that the first transducer 20 may complete at least one full rotation about the platen 10 without breaking the electrical connection between the first transducer 20 and the transducer controller 44. However, the controller 40 may operate the drive system 30 and the first transducer 20 or set of transducers by any other method; the controller 40 may further communicate with the drive system 30 and the first transducer 20 or set of transducers by any other means.

Figure 4:
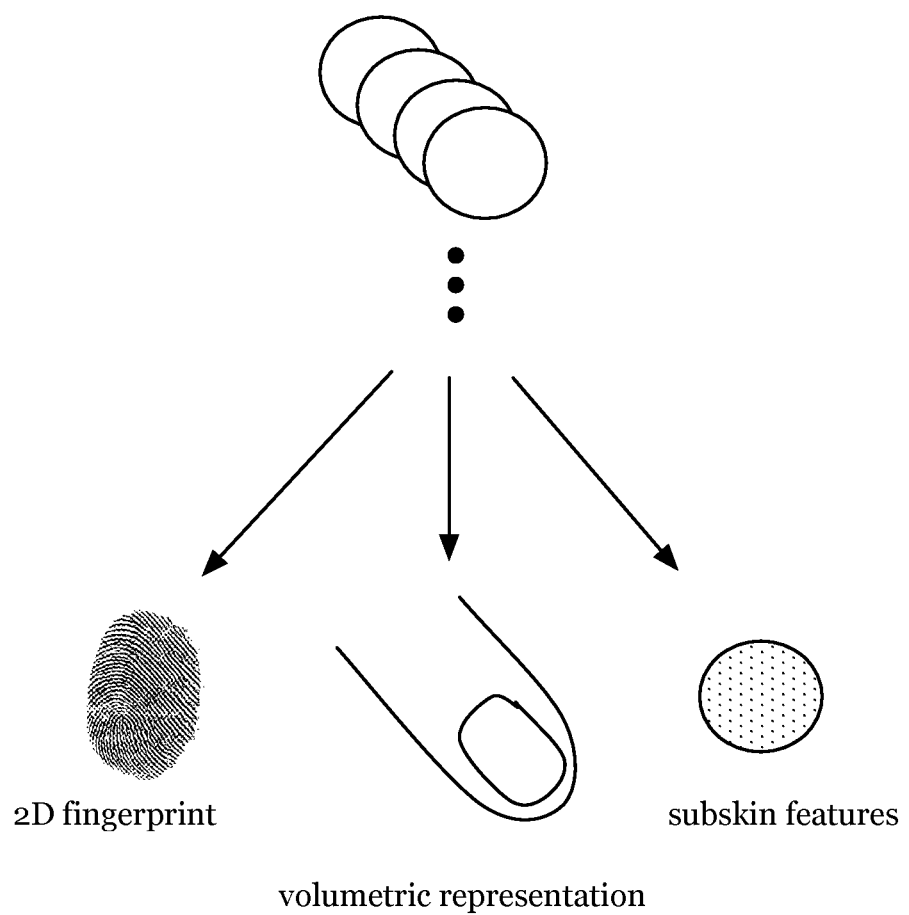
FIG. 4 is a schematic of example representations of a finger that may be created by the biometric sensor of a preferred embodiment.

The software module 50 of the preferred embodiment preferably functions to compose a form of the signals from the first transducer 20 into a representation of the finger 5. As shown in FIG. 1, the software module 50 preferably interfaces with an analog-to-digital (A/D) converter 52 that converts the received ultrasound data from an analog electrical signal to digital form, and a signal processor 54 that preferably performs digital signal processing such as filtering, noise reduction, compression of ultrasound data, and compiles the ultrasound data into a representation of the finger 5. However, the A/D converter 52 and/or the signal processor 54 may be integral with the processor 55 on which the software module 50 executes. The representation of the finger 5 is preferably a volumetric three-dimensional image formed by a plurality of B-scan ultrasound images, each of them formed by a plurality of pulse-echo A-scan images. As shown in FIG. 4, the three-dimensional representation may, for example, be compiled from a plurality of two-dimensional cross-sectional ultrasound images. The representation may alternatively be a two-dimensional image of a fingerprint, a selection of tissue and subsurface features of the finger 5, and/or an uncompiled set of two-dimensional B-scan or A-scans images. Cross-sectional images may be images of planes normal to the central axis of the platen 10, but may alternatively be planes at any angle relative to the central axis of the platen 10. The software module 50 may additionally and/or alternatively process biometric data obtained by other sensors such as infrared radiation sensors.

The software module preferably operates on a processor 55 arranged substantially proximal to the platen 10, such as within an encasement that houses the platen 10, first transducer 20, drive system 3o, and controller 40. For example, the biometric sensor may be a standalone device configured to collect ultrasound waves reflecting off of the finger 5 and to produce an image of the finger 5. Alternatively, the software module 50 may operate on a computer arranged substantially proximal to the platen 10. The computer may receive a form of the signals from the first transducer 20 via a wireless connection, such as a Wi-Fi or Bluetooth connection, or a wired connection, such as a USB 2.0 or RS-232 connection The software module 50 may access the form of the signals from the first transducer 20 or set of transducers once the data (form of the signals) is received by the computer; after the computer receives the data, the software module 50 may manipulate the data into the image of the finger 5. However, the software module may operate substantially remote from the platen 10, such as on a remote server or on a cloud-computing network. In a first example of the software module as a cloud-based service, the data (the form of the signals) may be transmitted to a remote server and where the data is manipulated to compose the image of the finger 5; a user may subsequently access the image of the finger 5 by opening an internet browser on a local computer and navigating to a specified website where the image of the finger is displayed or available for download. In a second example, the form of the signals from the first transducer 20 (such as the digital version of the converted analog signals from the first transducer 20) may be transmitted to a remote server, such as via an internet connection established by a network adapter connected to the biometric sensor or established by a computer in communication with the biometric sensor; the signals may then be manipulated into the image of the finger 5 by the software module operating on the remote server, and the image is preferably transmitted back to either the computer in communication with the biometric sensor or back to the biometric sensor itself. The software module 50 preferably compares the image of the finger 5 to at least one of a second image of a finger. The software module 50 may access the second image from a data storage device: arranged substantially proximal to the platen 10 (such as within the encasement); arranged within a computer arranged substantially proximal to the biometric sensor and in communication with the biometric sensor; or arranged remotely from the biometric sensor and in communication with the server on which the software module 50 operates. The software module 50 preferably compares the image of the finger 5 with the second image and determines whether the finger 5 from the image is the same as the finger from the second image. The results of the comparison are then preferably used to confirm the identity of the proprietor of the finger 5, such as by the biometric sensor or a user operating the biometric sensor, or by a computer connected to the biometric sensor or by a user operating the computer.

The signals from the first transducer 20 or set of transducers may be transmitted directly to a processor 55 or other device upon which the software module 50 operates, but may also pass through one or more additional devices or elements before a form of the signals reaches the software module 50. For example, analog signals may be transmitted from the first transducer 20 to the A/D converter 52 to be converted to digital signals; the signals may also pass through an amplifier to boost the signals or a filter to reduce noise in the signals; the signals may also be transmitted to the controller 40 where the signals are augmented with location information of the first transducer 20; or the signals may pass through any other suitable device or element before reaching the software module.

The biometric sensor may further include a user interface 60 that presents instructions and/or the representation of the inserted finger to a user. The instructions may, for example, include audio or visual text instructing a user to insert a finger, insert a specific finger ("insert right thumb"), how to insert a finger, or how to initiate a scan of the finger 5. The interface 60 may be a screen arranged substantially proximal to the platen 10 and the first transducer 20, such as within the encasement of the biometric sensor or a display connected to a computer in communication with the biometric sensor. The interface 60 may also be a screen arranged substantially remote from the biometric sensor, such as connected to the remote server or cloud-based network in communication with the biometric sensor. In the embodiment of the invention in which the software module compares the image of the finger 5 to a second image of a finger, the result of the comparison is preferably displayed on the interface.

The method of obtaining ultrasonic fingerprint imaging preferably includes receiving a finger on a platen 10 configured to receive the finger; moving a transducer to a first position; transmitting, ultrasonic waves toward the finger such that the ultrasonic waves interact with at least a portion of the finger; receiving the ultrasonic waves with the transducer after the ultrasonic waves interact with the finger; moving the transducer to a second position; generating signals based upon the received ultrasound waves; repeating the steps of transmitting ultrasonic waves, receiving the ultrasonic waves and generating signals based upon the received ultrasound waves; and composing a form of the signals into a three-dimensional representation of at least a portion of the surface tissue layer of the finger 5. The step of composing a form of the signals from the transducer into the image may be performed substantially remote from the platen 10, such as on a cloud-based network. The method may further comprise the step of be comparing the representation of the finger 5 to a second image of a finger, such as to identify the finger 5 as the same or different than the second finger. An additional step of composing a three-dimensional representation of at least a portion of a subsurface tissue layer of the finger may also be included in the preferred method, and the step of moving the transducer to a second position may include motivating the transducer arcuately and/or linearly about or along the finger 5, respectively. Finally, the method may include the step of displaying the representation of the finger on a display such that the representation may be viewed by a user.

As a person skilled in the art will recognize from the previous detailed description and from the figures and claims, modifications and changes can be made to the preferred embodiments of the invention without departing from the scope of this invention defined in the following claims.

We claim:

1. A biometric sensor system for generating a three-dimensional representation of a portion of a finger, the finger comprising a three-dimensional structure including a surface tissue layer and a subsurface tissue layer, the biometric sensor comprising:
   a platen configured to receive the finger;
   a first transducer arranged about the platen, configured to scan at least a portion of the finger by receiving ultrasound waves after the ultrasound waves reflect off of the finger, and further configured to output signals based upon the received ultrasound waves;
   a drive system configured to motivate the first transducer arcuately about a z-axis substantially parallel to the length of the finger to be scanned;
   a controller configured to control the motion of the drive system; and
   a software module configured to receive a form of the signals from the first transducer and to compose the form of the signals into a three-dimensional representation of at least a portion of the surface tissue layer of the finger wherein the software module is further configured to compose the form of the signals into a three-dimensional representation of at least, a portion of a subsurface tissue layer of the finger.

2. The biometric sensor of claim 1, wherein the platen is configured to receive a portion of the finger between the tip of the finger and the distal knuckle of the finger.

3. The biometric sensor of claim 1, further comprising a biased element arranged substantially proximal to the platen and configured to stabilize the finger on the platen such as that motion of the finger is minimized while the first transducer scans at least a portion of the finger.

4. The biometric sensor of claim 1, wherein the subsurface tissue layer of the finger is the dermis layer of the skin of the finger.

5. The biometric sensor of claim 1, wherein the software module is further configured to generate a two-dimensional image of a fingerprint by manipulating the three-dimensional image of the surface tissue layer of the finger.

6. The biometric sensor of claim 1, wherein the first transducer, drive system, control system, and software module are used to generate the signals and to compose a form of the signals into the representation of the finger by realizing principles of acoustic microscopy.

7. The biometric sensor of claim 1, wherein the software module is a cloud-based remote service.

8. The biometric sensor of claim 1, wherein the software module operates on a computer arranged substantially proximal to the platen and the form of the signals output by the first transducer is transmitted to the computer via a USB port arranged on the computer.

9. The biometric sensor of claim 1, further comprising:
 an encasement configured to house the platen, first transducer, drive system, and controller; and
 a processor arranged within the encasement and configured to communicate with the first transducer, the controller, and the drive system, and wherein the software module operates on the processor.

10. The biometric sensor of claim 1, further comprising a housing with inner wall arranged about the platen and an outer wall defining an enclosed internal space between the inner wall and the outer wall, wherein the first transducer is arranged within the internal space.

11. The biometric sensor of claim 10, wherein the internal space is filled with a coupling liquid that improves the propagation of ultrasound waves between the finger and the first transducer such that the first transducer is substantially submersed in the liquid throughout the arcuate motion of the first transducer within the internal space about the platen.

12. The biometric sensor of claim 11, further comprising a sliding seal that seals the coupling liquid in the internal space between the platen and the transducer.

13. The biometric sensor of claim 10, wherein at least a portion of the inner wall of the housing defines the platen.

14. The biometric sensor of claim 1, further comprising a rotor configured to communicate motion of the drive system to the first transducer.

15. The biometric sensor of claim 1, further comprising an encoder configured to communicate at least a portion of the position of the first transducer to the controller.

16. The biometric sensor of claim 15, wherein the software module is further configured to receive data pertaining to at least a portion of the position of the first transducer such that the software module composes the representation of the finger by pairing the form of the signals from the first transducer with the position of the first transducer.

17. The biometric sensor of claim 1, wherein the controller further comprises:
 a drive system controller that controls the motion of the drive system; and
 a transducer controller that controls the collection of the ultrasonic waves by the first transducer.

18. The biometric sensor of claim 17, wherein the first transducer is further configured to generate ultrasound waves and the transducer controller of the control system is further configured to excite the first transducer to generate ultrasound waves at a predetermined frequency.

19. The biometric sensor of claim 1, wherein the drive system comprises an electric motor having an output shaft in communication with the first transducer such that the first transducer is motivated arcuately about the central axis when the output shaft of the electric motor rotates.

20. The biometric sensor of claim 1, wherein the drive system is further configured to motivate the first transducer linearly substantially parallel to the central axis.

21. The biometric sensor of claim 20, wherein the drive system motivates the first transducer linearly to a first position and then arcuately about the central axis such that the first transducer receives ultrasound waves reflecting off at least a portion of a first circumference of the finger; subsequently, the drive system motivates the first transducer linearly to a second position and then arcuately about the central axis such that the first transducers receives ultrasound waves reflecting off at least a portion of a second circumference of the finger.

22. The biometric sensor of claim 20, wherein the drive system comprises a motor connected to a lead screw such that rotation of the motor induces the lead screw to rotate, which concurrently motivates the first transducer arcuately about the central axis and linearly substantially parallel to the central axis.

23. The biometric sensor of claim 1, wherein the first transducer is a piezoelectric transducer configured to generate and to receive ultrasound waves.

24. The biometric sensor of claim 1, further comprising a second transducer, arranged about the platen and substantially proximal to the first transducer, configured to generate ultrasound waves that reflect off of the finger and are then received by the first transducer.

25. The biometric sensor of claim 1, further comprising a second transducer, arranged about the platen and substantially proximal the first transducer, moving concurrently with the first transducer about the central axis, receiving ultrasound waves after the ultrasound waves interact with the finger, and outputting signals based upon the received ultrasound waves.

26. The biometric sensor of claim 25, wherein the software module is further configured to receive a form of the signals from the second transducer and to compose the representation of the finger based upon the form of the signals from both the first and second transducers.

27. The biometric sensor of claim 25, wherein the first and second transducers are identical.

28. The biometric sensor of claim 1, further comprising a user interface configured to direct a user in operating the biometric sensor.

29. The biometric sensor of claim 28, wherein the user interface is further configured to display the representation of the finger.

30. A biometric detection method for generating a three-dimensional representation of a portion of a finger, the finger comprising a surface tissue layer and at least one subsurface tissue layer and having an axis extending the length of the portion of the finger to be scanned, the biometric detection method including the steps of:
 receiving the finger on a platen configured to receive the finger;
 moving a first transducer to a first position;
 transmitting ultrasonic waves toward the finger such that the ultrasonic waves interact with at least a portion of the finger;
 receiving the ultrasonic waves with the first transducer after the ultrasonic waves reflect off of the finger;

generating signals based upon the received ultrasound waves;

moving the transducer about a z-axis substantially parallel to the length of the finger to a second position;

repeating the steps of transmitting ultrasound waves toward the finger, receiving the ultrasound waves after the waves reflect off of the finger, and generating signals based upon the received ultrasound waves; and composing a form of the signals into a three-dimensional representation of the at least one subsurface tissue layer of the finger.

31. The biometric detection method of claim 30, wherein the step of composing the signals into a three-dimensional representation of at least a portion of the finger is performed substantially remote from the platen.

32. The biometric detection method of claim 30, further comprising the step of comparing the representation of the finger to a second representation of a finger.

33. The biometric detection method of claim 30, further comprising the step of motivating the transducer around the circumference of the finger such the first transducer receives waves that reflect off at least a portion of the circumference of the finger.

34. The biometric detection method of claim 30, further comprising the step of motivating the transducer linearly along the length of the finger such that the transducer receives waves that reflect off at least a portion of the length of the finger.

35. The biometric detection method of claim 30, further comprising the step of displaying the representation of the finger on a display.

36. The biometric sensor of claim 1, wherein the central axis extends through the finger to be scanned.

37. The biometric sensor of claim 1, wherein the central axis is nearer the finger to be scanned than the first transducer.

38. The biometric sensor of claim 1, wherein the first transducer is motivated arcuately about the finger to be scanned.

39. The biometric sensor of claim 1, wherein the first transducer is motivated arcuately about the central axis along an arc having an interior facing the finger to be scanned.

* * * * *